US006803197B1

(12) United States Patent
Uitterlinden et al.

(10) Patent No.: US 6,803,197 B1
(45) Date of Patent: Oct. 12, 2004

(54) METHOD FOR DETERMINING SUSCEPTIBILITY TO BONE DAMAGE BY SCREENING POLYMORPHISMS IN THE VITAMIN D RECEPTOR GENE

(75) Inventors: Andreas Gerardus Uitterlinden, Poortugaal (NL); Johannes Petrus Thomas Maria Van Leeuwen, Amstelveen (NL); Huibert Adriaan Pieter Pols, Papendrecht (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 0 days.

(21) Appl. No.: 09/786,991

(22) PCT Filed: Sep. 10, 1999

(86) PCT No.: PCT/EP99/07719

§ 371 (c)(1),
(2), (4) Date: May 10, 2001

(87) PCT Pub. No.: WO00/15839

PCT Pub. Date: Mar. 23, 2000

(30) Foreign Application Priority Data

Sep. 10, 1998 (GB) .............................. 9819769

(51) Int. Cl.[7] .......................... C12Q 1/68; C12P 19/34; C07H 21/02; C07H 21/04
(52) U.S. Cl. ........................ 435/6; 435/91.2; 536/23.5; 536/24.31; 536/24.33
(58) Field of Search .......................... 435/6, 91.2, 810; 536/24.33, 24.31, 23.5

(56) References Cited

U.S. PATENT DOCUMENTS 5,593,833 A * 1/1997 Morrison et al. .............. 435/6
5,939,260 A * 8/1999 Spector et al. .................. 435/6

FOREIGN PATENT DOCUMENTS

WO    WO 94 03633    2/1994
WO    WO 97 40187    10/1997

OTHER PUBLICATIONS

Ahern, Jul. 1995, The Scientist, "Reagent Kits Offer Scientists . . . " pp. 1–5.*
Ralston, S.H. "The genetics of osteoporosis" QJ Med 1997; 90:247–251.*
Grant, et al., "Reduced bone density and osteoporosis associated with a polymorphic Sp1 binding site in the collagen type I alpha 1 gene," *Nature Genetics*, 14:203–205 (1996).

Uitterlinden, A.G., et al., "A large scale population based study of the association of vitamin D receptor gene polymorphisms with bone mineral density," *J Bone Miner Res*, 11:1242–8 (1996).
Uitterlinden, et al., "Relation of alleles of the collagen type I alpha1 gene to bone density and the risk of osteoporotic fractures in postmenopausal women," *New Engl J Med*, 338:1016–1021 (Apr. 9, 1998).
Uitterlinden, et al., "Sp1 binding site polymorphism in the cola1 gene is associated with BMD: the Rotterdam study," *Osteoporosis International*, Abstract 6(1):124, PSu164 (1996).
Uitterlinden, et al., "Vitamin D receptor genotype is associated with radiographic osteoarthritis at the knee," *J. Clin. Invest.*, 100(2):259–263 (1997).
Morrison, N.A., et al., "Prediction of bone density from vitamin D receptor alleles," *Nature*, 367:284–7 (1994).
Cooper, G.S., Umbach, D.M., "Are vitamin D receptor polymorphisms associated with bone density?," *J Bone Miner Res*, 11:1841–9 (1996).
White, C.P., et al., "Vitamin D receptor alleles predict osteoporotic fracture risk," Abstract, *J Bone Miner Res*, 9(suppll):S263 (1994).
Houston, L.A., Grant, S.F.A., Reid, D.M., Ralston, S.H., "Vitamin D receptor polymorphism, bone mineral density, and osteoporotic vertebral fracture: studies in a UK population," *Bone*, 18:249–52 (1996).
Ralston, "The Genetics of Osteoporosis," *Q J Med*, 90:247–251 (1997).
Ralston, "Genetic Markers of Bone Metabolism and Bone Disease," *Scand J Clin Lab Invest*, 57(Suppl. 227):114–121 (1997).

* cited by examiner

*Primary Examiner*—Carla J. Myers
*Assistant Examiner*—Sally Sakelaris
(74) *Attorney, Agent, or Firm*—Christensen O'Connor Johnson Kindness PLLC

(57) ABSTRACT

The present invention relates to a prognostic method and means for determining susceptibility to bone damage in a subject, by screening for polymorphisms in the Vitamin D receptor or collagen Iα1 genes. In particular, the method for determining susceptibility to bone damage comprises analyzing the genetic material of a subject to determine which of the B/b, A/a or T/t alleles of the restriction enzyme sites BsmI, ApaI and TaqI respectively are present. The method may further comprise determining which allele is present at die SpI restriction site of the collagen Iα1 gene. Specific combinations of the above alleles represent a haplotype which is associated with susceptibility to bone damage.

20 Claims, 1 Drawing Sheet

METHOD FOR DETERMINING SUSCEPTIBILITY TO BONE DAMAGE BY SCREENING POLYMORPHISMS IN THE VITAMIN D RECEPTOR GENE

The present invention relates to a prognostic method and prognostic means based on polymorphisms in the vitamin D receptor and collagen Iα1 genes. In particular, the present invention relates to a method for determining susceptibility to bone damage by screening for polymorphisms in vitamin D receptor or collagen Iα1 genes.

Osteoporosis is a common disease characterized by reduced bone mineral density (BMD), deterioration of bone micro-architecture and increased risk of bone damage, such as fracture.[1] It is a major public health problem which affects quality of life and increases costs to health care providers. In European populations, one in three women and one in twelve men over the age of fifty is at risk. The disease effects 25 million people in the USA, where the incidence of disease is 25% higher than it is in the UK, and a further 50 million people in Japan and Europe combined. It is estimated that by the middle of the next century the number of osteoporosis sufferers will double in the West, but may increase six-fold in Asia and South-America. Fracture is the most serious endpoint of osteoporosis, particularly fracture of the hip which affects up to 1.7 million people worldwide each year. It is estimated that by the year 2050, the number of hip fractures worldwide will increase to over 6 million, as life expectancy and age of the population increase.

Treatment of osteoporosis is unsatisfactory. In particular, once bone damage has occurred as a result of osteoporosis, there is little a physician can do other than let the bone heal. In the elderly, this may be a slow and painful process. Diagnosis of those at risk of developing osteoporosis allows more effective preventative measures. Strategies for the prevention of this disease include development of bone density in early adulthood, and minimisation of bone loss in later life. Changes in lifestyle, nutrition and hormonal factors have been shown to affect bone loss.[7-14]

Osteoporosis can be considered a complex genetic trait with variants of several genes underlying the genetic determination of the variability of the phenotype. Low bone mineral density (BMD) is an important risk factor for fractures, the clinically most relevant feature of osteoporosis. Segregation analysis in families has shown that BMD is under polygenic control[12,13] while, in addition, biochemical markers of bone turnover have also been shown to have strong genetic components[14-16]. Several candidate genes have been analysed in relation to BMD but the most widely studied gene in this respect, the vitamin D receptor (VDR) gene, explains only a small part of the genetic effect on BMD[8]. Numerous studies, focussing on the BsmI allele of the vitamin D receptor gene have concluded that absence of the restriction site correlates with low bone mineral density. Most genetic analyses have focussed on BMD as a determinant of fracture risk and not so much on fractures themselves as an endpoint in the analysis. Recently, an SpI polymorphism in the COLIA1 gene encoding the most abundant bone matrix protein, was found to be associated with reduced BMD and, more importantly, also with increased risk of osteoporotic fracture[9,10]. An emerging theme from these studies seems to be the association of the absence of the BsmI restriction site with reduced bone mineral density, which in turn signifies increased risk of bone damage such as fracture.

Few studies have addressed genetic association with the clinically most important endpoint of osteoporosis, namely bone damage, in particular fracture. Accordingly, it is an object of the present invention to improve the prognosis of predisposition or susceptibility to bone damage.

In a first aspect of the present invention, there is provided a method of determining susceptibility to bone damage in a subject, said method comprising analyzing genetic material of a subject to determine which allele(s) of the vitamin D receptor gene is/are present.

Thus, the present invention satisfies the pressing need for identification of those individuals susceptible to bone damage, thus facilitating the development of preventative measures. For example, those at risk may avoid damage by modifying their lifestyle and implementing bone strengthening measures, such as regular exercise and a healthy diet. Typically, the method of the present invention comprises analysis of polymorphisms in the VDR gene to determine susceptibility to bone damage. The method may include determining whether one or more particular alleles are present, or which combination of those alleles (i.e. the haplotype) is present. The method may further comprise determining whether subjects are homozygous or heterozygous for alleles or haplotypes of the vitamin D receptor gene.

Vitamin D is a potent regulator of bone and calcium homeostasis, as well as of cellular differentiation and replication in many tissues, and mediates its effects through the vitamin D receptor (VDR). Cloning of the vitamin D receptor has shown it to be a member of the ligand-activated superfamily, which are natural regulators of a number of physiological and developmental processes. Evidence suggests that the vitamin D receptor activates expression of the osteocalcin gene through interaction with a palindromic sequence in the promoter of the gene.[27] The osteocalcin gene product is a marker of bone turnover in normal and disease states, and inter-individual variation in its circulating levels have been associated with polymorphisms in the vitamin D receptor gene.

The vitamin D receptor gene (12q12) comprises inherited polymorphisms between exon 7 and the 3' UTR of the VDR gene, as shown in FIG. 1. These alleles are denoted B/b, A/a and T/t for restriction enzyme sites BsmI, ApaI and TaqI respectively (or enzymatic or chemical procedures having similar specificity), where a lower case letter denotes the presence of a wild type restriction site which is capable of being cleaved, and a capital letter denotes the presence of a mutant restriction enzyme site which is not capable of being cleaved by the relevant restriction enzyme. For the purposes of the present invention, determination of which alleles are present in a particular gene may be referred to as determining the genotype of a subject for a particular gene. It is apparent from the above that each copy of the vitamin D receptor gene will comprise a specific combination of the three alleles, this combination being referred to as the haplotype of the gene. For example, the haplotype may be baT, indicating the presence of cleavable BsmI and ApaI sites, and a non-cleavable TaqI site. Direct haplotyping of the VDR gene has allowed five different haplotypes to be determined, of which three are common.[11]

The present invention is based upon the surprising observation of a correlation between the presence of the b allele of the vitamin D receptor and susceptibility to/or risk of (where the terms are used interchangeably) bone damage, such as fracture. The invention goes further to show that presence of the a and/or T alleles, and in particular the haplotype baT is/are associated with increased risk of bone damage. A subject having the baT haplotype may show a higher risk of fracture compared to a subject having the bAt, or BAt haplotype which confers the lowest risk of fracture. The results are unexpected, as previous studies have shown the b allele, and particularly the baT haplotype, to be associated with high bone density, which itself is not associated with fracture risk. Thus, in contrast to previous results, the present inventions have shown that susceptibility to bone damage is independent of bone mineral density in a subject. By screening for the presence of alleles of the vitamin D receptor gene, susceptibility to bone damage may be assessed without the need for analysis of bone mineral density.

Preferably, the method of the first aspect of the present invention further comprises determining whether the alleles present are associated with risk of bone damage. This may be performed by comparing the alleles present in a subject with those known to be associated with risk of bone damage. For example, a visual aid detailing alleles and the relative risk of bone damage associated therewith may be used to determine whether the genotype of the subject is associated with a high or low risk of bone damage.

The first aspect of the present invention may also comprise the additional step of determining aspects of calcium metabolism, such as calcium levels in a subject. Preferably, the daily calcium intake is measured. This feature of the first aspect is based on the observation that the correlation between vitamin D receptor genotype and bone damage may be dependent upon dietary calcium intake. Specifically, in subjects having low calcium intake, genotype dependent risks may be greater.

The method of the present invention may be performed in vitro. Preferably, the method is performed on tissue or fluid removed from the body of the subject. Thus, the present invention relates to a non-invasive diagnostic method, the results of which provide an indication of susceptibility to bone damage but do not lead to a diagnosis upon which an immediate medical decision regarding treatment has to be made.

The present invention may be performed on any subject for whom it is desirable to determine risk of bone damage. Preferably, the subject may be a mammal. Most preferably, the subject is a human, preferably a female.

Bone damage may be any form of structural damage including fractures, breaks, or chips. The term may also include biological degradation or deterioration of bone. Typically, the term bone damage does not include low bone density. This is in line with the finding that risk of bone damage is independent of bone density. Fracture may be defined as the clinically most important endpoint, and thus the method of the first aspect of the invention preferably relates to a method of determining risk of fracture. Although such bone damage will usually be the result of osteoporosis, it is irrelevant for the purposes of the present invention whether a subject has first been diagnosed as having osteoporosis.

In a preferred feature of the first aspect of the present invention, there is provided a method of determining susceptibility to bone damage, said method comprising analysing the genetic material of a subject to determine which of the B/b, A/a or T/t alleles of the vitamin D receptor are present. The method may comprise determining whether more than one of the above alleles is present. The subject may be further classified as heterozygous or homozygous for one or more of these alleles. Preferably, the method comprises the additional step of determining whether the allele (s) present are associated with risk of bone damage, wherein presence of the b or a alleles is associated with increased risk of bone damage, and presence of the t allele is associated with reduced risk of bone damage. Homozygosity for the a or b allele may further increase the susceptibility to bone damage in a subject, while homozygosity for the t allele may further decrease susceptibility.

In a preferred feature of the first aspect of the present invention, there is provided a method of determining susceptibility to bone damage in a subject, said method comprising analysing the genetic material of a subject to determine the haplotype of the BsmI, ApaI and TaqI alleles at the vitamin D receptor. Preferably, said method comprises determining whether the haplotype of the subject is associated with risk of bone damage, wherein the haplotype baT is associated with high risk of bone damage. A subject homozygous for said haplotype may be at a higher risk of bone damage than those heterozygous for the haplotype.

In a preferred feature of the first aspect, there is provided a method of determining susceptibility to bone damage, said method further comprising analysing the genetic material of a subject to determine which allele of the collagen I$\alpha$1 (17q22) gene is present. An allele in this gene may be denoted by S/s, where s indicates the presence of a G to T polymorphism at the SpI restriction site. This feature of the present invention is based on the observation that the correlation between increased fracture risk and VDR genotype may be collagen I$\alpha$1 genotype dependent. Specifically, in those subjects having vitamin D receptor alleles indicating risk of bone damage, the risk may be increased in those subjects also carrying a G to T polymorphism at the SpI site of the collagen I$\alpha$1 gene.

In a preferred feature of the first aspect, there is provided a method of determining susceptibility to bone damage, said method comprising determining the copy number of the B/b, A/a or T/t alleles or haplotype of the vitamin D receptor gene and/or the S/s alleles of the collagen I$\alpha$1 gene, where an increase in copy number is associated with increased risk of bone damage.

The present invention may be performed using any suitable method known in the art. Preferably, a tissue or fluid sample is first removed from a subject. Examples of suitable samples include blood, mouth or cheek cells, and hair samples containing roots. Other suitable samples would be known to the person skilled in the art. The genetic material is then extracted from the sample, using any suitable method. The agenetic material may be DNA or RNA, although preferably DNA is used. For example, the DNA may be extracted using the technique described in Sambrook et al (Molecular Cloning—A Laboratory Manual, Cold Spring Harbor Laboratory Press). Determination of the genotype of a subject may then be carried out using the extracted DNA, employing any one of the following techniques:

Southern blot analysis following digestion with one or more appropriate restriction enzymes.

PCR amplification followed by digestion with one or more appropriate restriction enzymes and, optionally, separation of digestion products by gel electrophoresis.

Sequencing of a relevant gene fragment by any suitable method.

Visualization of heteroduplex patterns, for example on PAA or agarose gels, where different patterns may indicate the presence of one or more specific alleles.

Separation of DNA fragments using denaturing gradient gels, wherein the degree of separation will depend upon the presence or absence of one or more polymorphic restriction sites.

Separation using SSCP analysis, the patterns of which will depend upon the presence or absence of one or more polymorphic restriction sites.

Use of allele specific oligonucleotides, hybridization patterns of which will be specific for various combinations of alleles.

Methods such as OLA, Taqman or dot-blot for the detection of known mutations.

Visualization of DNA sites using fluorescent labelled probes for alleles of interest.

RFLP analysis.

Where it is desirable to use particular restriction enzymes in performing the present invention, the skilled person will understand that enzymatic or chemical procedures having similar specificities may also be used. For example, restriction enzymes having similar specificity (isoschizomers) to those described herein may be used, or chemical degradation procedures with DNA or RNA cutting specificity.

Other techniques suitable for determining the genotype of a subject may be used in the present invention.

Where the haplotype of a gene is to be determined, it is preferable to use a direct haplotyping method, as described in Uitterlinden et al[11]. In such a method, the relevant portion of the gene is amplified and then subjected to restriction enzyme digestion, in order to determine the presence or absence of restriction enzyme sites. Thus, for example, where the haplotype of the vitamin D receptor gene is to be determined, the portion of the gene between exon 7 and the 3' UTR may be amplified, and the amplified DNA digested with the BsmI, ApaI or TaqI restriction enzymes. Gel analysis may then be used to determine which alleles are present.

Preferably, a fragment may be amplified using polymerase chain reaction (PCR) techniques, to produce copies which, where the fragment is of the vitamin D receptor, are at least 1000 base pairs in length, and most preferably at least 1800 base pairs in length. Where the fragment to be amplified is of the collagen Iα1 gene, PCR primers may be selected to amplify a fragment which is at least 50 base pairs in length, preferably at least 200 base pairs in length. PCR techniques are well known in the art, and it is within the ambit of the skilled person to identify primers for amplification of the appropriate region of the above genes, namely the region from exon 7 to the 3' UTR of the vitamin D receptor gene and the first intron of the collagen Iα1 gene. PCR techniques are described in EP-A-0200362 and EP-A-0201184.

In a preferred feature of the first aspect, there is provided a method of determining susceptibility to bone damage in a subject, said method comprising amplifying a fragment comprising a portion of the region from exon 7 to the 3' UTR of the vitamin D receptor gene, and determining which allele(s) in the vitamin D receptor is/are present. Primers suitable for amplification of said portion of the vitamin D receptor gene would be readily available to a person skilled in the art Examples of such primers include:

1. 5'-CAACCAAGACTACAAGTACCGCGTCAGTGA-3' (SEQ ID NO:1) and/or
2. 5'-GCAACTCCTCATGGCTGAGGTCTC-3' (SEQ ID NO:2)

In features of the present invention where it is desirable to determine which allele of the collagen Iα1 gene is present, at least a portion of the first intron of the collagen Iα1 gene may be amplified, followed by determination of the presence of a SpI restriction site. Suitable primers include:

1. 5'-TAACTTCTGGACTATTTGCGGACTTTTTGG-3' (SEQ ID NO:3) and/or
2. 5'-GTCCAGCCCTCATCCTGGCC-3' (SEQ ID NO:4)

Additional primer sequences are described in Grant et al[9].

Where the amplified portion of the gene is larger than the above defined portions of the genes containing the relevant alleles, it is preferable to avoid the inclusion of vitamin D receptor or collagen Iα1 gene sequences which comprise any one of the BsmI, ApaI or TaqI restriction sites of the vitamin D receptor gene, or the SpI site of the collagen Iα1 gene.

In a second aspect of the present invention, there is provided a method of therapy, said method comprising treating a subject diagnosed as being at risk of bone damage, to reduce the risk of bone damage. Preferably, the subject is diagnosed as being at risk of bone damage in accordance with the first aspect of the present invention.

Therapy may in the form of preventative or palliative care. Suitable treatments include modifications to lifestyle, regular exercise and changes in diet to strengthen bones, and hormone therapy. Suitable treatments, including pharmaceutical preparations to reduce bone loss, would be known to physicians and persons skilled in the art. Examples include anabolic steroids, bisphosphonates, vitamin D preparations, calcium supplements and Hormone Replacement Therapy.

In a third aspect of the present invention, there is provided a method of predicting the response of a subject to treatment, said method comprising analysing genetic material of a subject to determine which allele(s) of the vitamin D receptor gene and/or collagen Iα1 gene is/are present. Preferably, the method includes determining whether the subject is susceptible to bone damage. Where a subject has been determined as susceptible to bone damage, the method may further comprise administering the appropriate treatment. The effect of a therapeutic or preventative agent may depend on the underlying cause of the heart disease, and in some cases it may be preferable to avoid the use of certain treatments. This aspect of the present invention may also be useful for identifying agents which may be used in the treatment of bone damage.

In a fourth aspect of the present invention, there is provided use of a kit to determine which allele(s) of the vitamin D receptor gene and/or collagen Iα1 gene is/are present, said kit comprising (i) one or more nucleic acid primer molecules for amplification of a portion of the vitamin D receptor and/or collagen Iα1 genes, and (ii) means for determining which allele(s) is/are present in said genes.

Preferably, the primer molecules are suitable for amplification of at least a portion of the region between exon 7 and the 3' UTR of the vitamin D receptor gene, and/or a portion of the first intron of the collagen Iα1 gene. Examples of suitable primers are described above.

Means for determining which allele(s) is/are present in the vitamin D receptor gene, and/or collagen Iα1 gene may include any reagents or molecules necessary for use in any of the methods described above. For example, where PCR followed by DNA digestion is used, said means preferably include PCR reagents and one or more of the BsmI, ApaI, TaqI or SpI restriction enzymes. Where the method employs Southern Blotting, heteroduplex visualization, or fluorescent labelling techniques for example, probes which bind to the appropriate regions of the vitamin D receptor gene, and/or collagen Iα1 gene may be included. Where necessary, such probes may be labelled to allow detection, for example by nick-translation, radio- or fluorescent-labelling, or random primer extension whereby the non-labelled nucleotides serve as a template for the synthesis of labelled molecules. Other methods of labelling probes are well known in the art.

In a preferred feature of the fourth aspect of the present invention, there is provided use of a kit further comprising means for indicating correlation between the genotype of a subject and risk of bone damage. Said means may be in the form of a chart or visual aid, which indicate that presence of the b allele or baT haplotype, and the S allele of the couagen Iα1 gene is associated with increased fracture risk.

In a fifth aspect of the present invention, there is provided a kit for determining risk of bone damage in a subject, said kit comprising (i) one or more nucleic acid primer molecules for amplification of a portion of the vitamin D receptor and/or collagen Iα1 genes; (ii) means for determining which allele(s) is/are present in said genes; and (iii) means for indicating correlation between the allele(s) and risk of bone damage.

In a preferred feature of the fifth aspect, the kit may also comprise DNA control samples, for comparison with DNA sequences of a subject. The control samples may comprise the sequence of one or more alleles of the vitamin D receptor or collagen Iα1 genes, or may comprise the sequence of various haplotypes.

Preferred features of each aspect of the present invention are as for each other aspect, mutatis mutandis.

The present invention will now be described in detail with reference to the following examples and figures.

EXAMPLE 1

Figure 1:
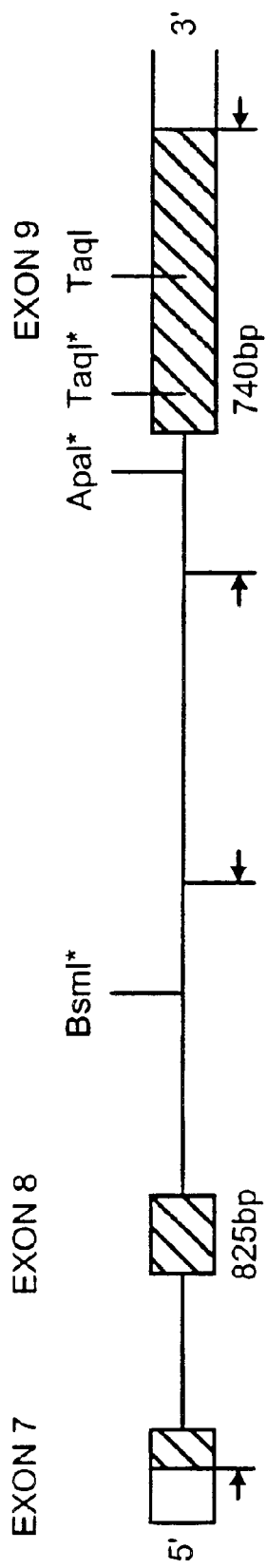
FIG. 1 is a schematic presentation of the region between exon 7 and the 3' UTR of the vitamin D receptor genes.

Interaction Between the Vitamin D Receptor Gene and Collagen Type I1 Gene in Determining Susceptibility for Osteoporotic Fracture in Postmenopausal Women In a large population-based study 97 fracture cases were recorded among 1004 postmenopausal women aged 55–80 years. We found a VDR haplotype, constructed from three adjacent restriction fragment length polymorphisms (RFLPs)[11] to be over-represented among fracture cases (p=0.009) corresponding to a Relative Risk of 1.8 (95% confidence interval 1.0–3.3) for heterozygous carriers and 2.6 (95%CI 1.4–5.0) for homozygous carriers of the risk haplotype. The effect was similar for vertebral and nonvertebral fractures and, most importantly, independent of BMD. We observed significant interaction (p=0.03) between VDR and COLIA1 genotype effects. Fracture risk was not VDR genotype-dependent in the COLIA1 "reference" group (genotype GG) while in the COLIA1 "risk" group (genotypes GT and TT) the relative risk of fracture was 2.1 (95%CI 1.0–4.4) for heterozygous and 4.4 (95%CI 2.0–9.4) for homozygous carriers of the VDR risk haplotype. We conclude that both the VDR and COLIA1 polymorphisms are genetic markers for osteoporotic fracture in women, independent of BMD. Our data indicate that interlocus interaction is likely to be an important component of osteoporotic fracture risk.

We first analysed the relation between fractures and VDR genotype and, second, studied interaction between the VDR and the COLIA1 polymorphisms.

For COLIA1 we investigated the SpI G to T polymorphism[9] in relation to haplotypes constructed of three adjacent restriction fragment length polymorphisms (RFLPs) in the VDR gene, i.e. for BsmI, ApaI, and TaqI, respectively[11]. When we analysed the distribution of fractures in women grouped according to VDR genotype we observed an over-representation of fractures in women carrying the haplotype 1 (Table 1). Women were subsequently grouped according to carrier status for this VDR haplotype as heterozygous carriers (including the genotypes 12 and 13) and homozygous carriers (consisting of genotype 11) of the risk haplotype and compared to women not carrying the haplotype (including genotypes 22, 23, and 33). No significant differences in known risk factors for osteoporosis could be observed between women grouped according to VDR haplotype 1 (Table 2). Similar results were obtained when the women were grouped according to VDR haplotypes 2 or 3 (data not shown).

We then went on to determine the distribution of fractures in women according to their carrier status for VDR haplotype 1 (Table 3). Significantly more women heterozygous for VDR haplotype 1 had fractures than the women in the reference group and for women homozygous for the VDR haplotype 1 this difference further increased. When women were grouped according to VDR haplotype 2, we observed an under-representation in fracture cases (p=0.002) while for VDR haplotype 3 no differences were observed (p=0.65; data not shown). Logistic regression analysis showed that women heterozygous for the VDR haplotype 1 had 1.8 times the risk for fractures compared to women in the reference group. This was further increased for women homozygous for the VDR haplotype 1 to 2.6 times the risk for fracture compared to women in aft the reference group (Table 3). When we analyzed by type of fracture we observed the VDR genotype effect to be similar for vertebral fracture cases (p=0.07) and non-vertebral fracture cases (p=0.04; data not shown). The relative risk of fracture did not essentially change after adjustment for potential confounding factors such as age, weight, and bone density in the multivariate regression analysis.

In this group of women we also determined the distribution of fractures according to COLIA1 genotype (Table 3). In correspondence with what we previously found[10] we observed the COLIA1 T allele to be associated with increased fracture risk, independent of BMD. To assess whether there was interaction between the VDR haplotype effect and the COLIA1 genotype effect on fracture we determined the distribution of fractures according to VDR haplotype 1 in the different COLIA1 genotype groups (Table 4). The distribution of fracture cases according to the VDR genotype did not differ in the group of women with the COLIA1 GG genotype. However, in the COLIA1 risk groups of women with the GT and TT genotypes the distribution of fractures cases was strongly VDR genotype dependent (Table 4). Logistic regression analysis showed that the effect of VDR genotype on fracture risk is absent in women with the COLIA1 GG genotype while the VDR genotype effect is large in the COLIA1 hetereozygous GT and homozygous TT risk group (Table 4). When age, VDR genotype, COLIA1 genotype and fracture were considered together in a multivariate regression model we genotype significantly modified the COLIA1 genotype effect (p=0.03 for the interaction term). The effect was found to be similar for nonvertebral fracture cases and vertebral fracture cases and when bone density was entered into the model the results did not change indicating the interaction effect to be independent of bone density.

Although VDR gene polymorphisms have been implicated in the genetic regulation of BMD[7], a meta-analysis showed that the effects on BMD are small[8] as we also demonstrated earlier in our study population[11]. While an early unpublished report suggested VDR to predict osteoporotic fracture in older Australian women[17], no associations with osteoporotic fracture have been reported in two studies published until now on the relation of VDR with fracture[18,19]. These studies were small, however, and used only the BsmI RFLP in their analysis. Our findings suggest the VDR to be involved in bone metabolic pathways other than those reflected in BMD but still leading to increased fracture risk. The VDR genotype dependent increased fracture risk is especially pronounced in interaction with COLIA1 genotype of which we already reported the COLIA1 SpI "T" allele to increase fracture risk in our study population[10]. The epistatic interaction between VDR and COLIA1 genotype we here describe points to biological interactions of the gene products. The VDR is a member of the steroid transcription factors, known to be important regulators of gene expression. Vitamnin D dependent regulation of expression of bone-specific genes, such as osteocalcin, has been well documented[22] and also includes regulation of the expression of the collagen type I1 at the level of transcription[20,21]. In RT-PCR experiments the SpI polymorphism has been shown to lead to differential binding affinity of the SpI transcription factor[9] and also to genotype dependent COLIA1 mRNA expression levels[23]. Therefore, while the exact molecular mechanism underlying the associations we here describe remains to be elucidated, the VDR regulated expression of the collagen type I1 gene could be an important factor in the synergistic interaction we observed and may differ across VDR alleles.

It is likely that interactions between genetic loci involved in a complex trait are a common phenomenon and several examples have already been demonstrated but mostly in model organisms. Our data represent the first example of interlocus interaction in relation to fractures between two well known candidate genes in osteoporosis, a complex trait in humans. We show that the interaction leads to increases in the risk of fracture, the clinically most relevant feature of osteoporosis, and that this increase in risk is independent of BMD, the most widely used diagnostic criterium for osteoporosis. This has important consequences not only for the analysis of the genetic basis of osteoporosis but also for the identification of individuals at risk of the disease. Finally, it also raises the possibility of developing new therapeutic intervention strategies based on the known involvement of the VDR and the COLIA1 gene in bone metabolism.

Methods

Study subjects. The Rotterdam Study is a population-based cohort study of 7983 subjects aged 55 or more years, residing in the Ommoord district of the city of Rotterdam in the Netherlands. The study was designed to document the occurrence of disease in the elderly in relation to several potential determinants[24]. A total of 10,275 persons, of whom 9161 (89 percent) were living independently, were invited to participate in the study in 1991. In the independently living subjects, the overall response rate was 77 percent for home interview and 71 percent for examination in a research centre, including measurement of anthropometric characteristics, bone mineral density and blood sampling. The Rotterdam Study was approved by the Medical Ethics Committee of the Erasmus University Medical School and written informed consent was obtained from each subject. The analysis of the association between COLIA1 genotype, VDR genotype and osteoporotic fracture was performed in a subgroup of women participating in the study. Baseline measurements of bone mineral density were available for 5931 independently living subjects from the study, but 1453 of these were excluded on the basis of age (>80 yrs), use of a walking aid, diabetes mellitus or use of diuretic, estrogen, thyroid hormone or cytostatic drug therapy. From the 4478 remaining subjects, we studied a random sample of 1500 women aged 55 to 80 years. Anthropometric data, DNA samples or genotype data for both loci were not available for 481 women, and we excluded women with the rare VDR haplotypes 4 and 5 (n=15) resulting in a final study group of 1004 women.

Measurements. Height and weight were measured at the initial examination. Bone mineral density (in $g/cm^2$) was determined by Dual Energy X-ray Absorptiometry (Lunar DPX-L densitometer; Lunar Corporation, Madison, Wis., USA) at the femoral neck and lumbar spine (vertebrae L2 to L4) as described elsewhere.[25] Dietary intakes of calcium (mg/day) during the preceding year were assessed by food frequency questionnaire and adjusted for energy intake. Age at menopause and current cigarette smoking were assessed by questionnaire. For 732 women (73 percent), lateral radiographs of the spine from the fourth thoracic to the fifth lumbar vertebrae were obtained at baseline examination and analysed for the presence of prevalent vertebral fractures by morphometric analysis as previously described.[26] The occurrence of incident non-vertebral fractures, including hip, wrist and other fractures, were recorded, confirmed and classified by a physician over a mean follow-up period of 3.8 years. In total, 49 prevalent vertebral fracture cases and 52 incident non-vertebral fracture cases were recorded (7 hip, 6 upper humerus, 22 wrist, 4 hand, 4 ankle, 3 foot, and 5 other fractures). Four subjects, in which both a vertebral and a nonvertebral fracture were present, were each counted as one fracture case, resulting in 97 cases with one or more fractures.

Determination of COLIA1 and VDR genotypes. Genomic DNA was extracted from peripheral venous blood samples according to standard procedures and the polymorphism in the COLIA1 gene was detected by PCR with a mismatched primer that introduces a di-allelic restriction site, as previously described.[9] The test discriminates two alleles named S and s, corresponding to nucleotides G and T, respectively at the first base of the SpI binding site in the first intron of the gene for COLIA1. Three anonymous polymorphic restriction enzyme recognition sites at the 3' end of the VDR gene, i.e. for BsmI, ApaI and TaqI were assessed in relation to each other by a direct molecular haplotyping PCR procedure which we developed[11]. This allowed us to determine phase of the alleles at each of the RFLP loci and as a result three frequent haplotype alleles are discerned, encoded 1 (baT; frequency 48%), 2 (BAt;40%), and 3 (bAT;10%) combining to 6 genotypes encoded 11, 12, 13, 22, 23, and 33. We excluded the less frequent haplotypes 4 and 5 from the analysis. Women with genotypes containing these haplotypes (n=15) represent 1.5% of this population. Detailed information on haplotype alleles and genotype frequencies in the Rotterdam Study can be found elsewhere[11].

Statistical Analysis. Clinical variables were compared between the genotype groups by analysis of covarianace to adjust for confounding factors. For the comparisons we made reference, heterozygote and homozygote groups for each of the COLIA1 and VDR alleles. For COLIA1 the groups comprised the GG genotype group for the reference group, GT for the heterozygote risk group and TT for the homozygote risk group. For VDR haplotype 1 the groups comprised genotypes 22, 23, and 33 for the reference group, genotypes 12, and 13 for the heterozygote risk group, and genotype 11 for the homozygote risk group. The Chi-squared test was used to test for genotype distribution in women with and without fractures. Odds ratios (with 95 percent confidence interval) were calculated by multivariate logistic regression analysis to estimate the relative risk of osteoporotic fracture by genotype. For regression analysis using combinations of VDR and COLIA1 genotype we defined the "reference" group to include women with the COLIA1 GG genotype in combination with the VDR 22, or 23 or 33 genotype. The regression analysis included an interaction term defined as VDR genotype multiplied with COLIA1 genotype. All p-values for statistical tests were two-sided.

TABLE 1

Number of postmenopausal women with fractures according to VDR Genotype

| VDR Genotype | No. with fracture/total No. (%) |
|---|---|
| 11 | 34/255 (13.3) |
| 12 | 35/375 (9.3) |
| 13 | 13/101 (12.9) |
| 22 | 7/179 (3.9) |
| 23 | 6/82 (7.3) |
| 33 | 2/12 (16.7) |
| Chi2 | 13.3 |
| P Value | 0.04 |

TABLE 2

Characteristics of 1004 postmenopausal women according to their VDR haplotype 1 genotype

| | VDR genotype[+] | | | |
|---|---|---|---|---|
| Characteristic* | Reference (n = 273) | Heterozygotes (n = 476) | Homozygotes (n = 255) | P Value |
| Age (yr) | 66.4 ± 7.0 | 67.4 ± 7.0 | 67.1 ± 6.7 | 0.19 |
| Height (cM) | 162.3 ± 6.3 | 162.1 ± 6.0 | 161.7 ± 7.5 | 0.66 |
| Weight (Kg) | 68.9 ± 9.7 | 68.6 ± 10.5 | 69.3 ± 10.5 | 0.70 |
| Age at Menopause (yr) | 49 ± 5 | 49 ± 5 | 49 ± 5 | 0.35 |
| Dietary calcium intake (mg/day) | 1076 ± 335 | 1103 ± 329 | 1073 ± 287 | 0.42 |
| Current smoker (%) | 20 | 21 | 24 | 0.51 |
| Femoral Neck Bone Mineral Density (g/cm$^2$) | 0.82 ± 0.15 | 0.80 ± 0.12 | 0.81 ± 0.13 | 0.21 |

*Plus-minus values are means ± SD
[+]"Reference" includes VDR genotypes 22, 23, 33; "Heterozygotes" includes 12, 13; "Homozygotes" includes 11

TABLE 3

Number of postmenopausal women with fractures and Odds Ratio for fracture according to VDR halotype 1 genotype and according to COLIA1 genotype

| | Fracture | | |
|---|---|---|---|
| | No. with fracture/ | Odds Ratio (95% CI) | |
| Genotype[+] | total No. (%) | Age-adjusted | Multivariate* |
| a. By VDR haplotype 1 genotype | | | |
| Reference | 15/273 (5.5) | 1.0 | 1.0 |
| Heterozygotes | 48/476 (10.1) | 1.8 (1.0–3.3) | 1.6 (0.8–3.1) |
| Homozygotes | 34/255 (13.3) | 2.6 (1.4–5.0) | 2.4 (1.2–4.8) |
| Chi2 | 9.47 | — | — |
| P Value | 0.009 | | |
| b. By COLIA1 genotype | | | |
| GG | 53/679 (7.8) | 1.0 | 1.0 |
| GT | 37/293 (12.6) | 1.7 (1.1–2.7) | 1.6 (1.0–2.6) |
| TT | 7/32 (21.9) | 3.7 (1.5–9.2) | 3.3 (1.3–8.4) |
| Chi2 | 11.1 | — | — |
| P Value | 0.004 | | |

[+]"Reference" includes VDR genotypes 22, 23, 33; "Heterozygotes" including 12, 13; "Homozygotes" including 11
*Multivariate Odds Ratios were adjusted for age, weight, and femoral neck BMD.

TABLE 4

Number of postmenopausal women with fractures and Odds Ratios for fractures according to combined VDR haplotype 1 and COLIA1 genotype

| | COLIA1 genotype | | | |
|---|---|---|---|---|
| VDR genotype* | GG | GT | TT | GT + TT |
| a. Number with Fractures/total number (%) | | | | |
| Reference | 13/194 (6.7) | 2/70 (2.9) | 0/9 (0) | 2/79 (2.5) |
| Heterozygotes | 27/315 (8.6) | 18/149 (12.1) | 3/12 (25.0) | 21/161 (13.0) |
| Homozygotes | 13/170 (7.6) | 17/74 (23.0) | 4/11 (36.4) | 21/85 (24.7) |
| Chi2 | 0.59 | 13.3 | 3.94 | 17.3 |
| P Value | 0.74 | 0.001 | 0.14 | 0.0002 |
| b. Age-adjusted Odds Ratio (95% Cl)* | | | | |
| Reference | 1.0 | 0.4 (0.1–2.0) | —¶ | 0.4 (0.1–1.8) |
| Heterozygotes | 1.3 (0.6–2.5) | 1.9 (0.9–4.1) | 4.8 (1.1–21) | 2.1 (1.0–4.4) |
| Homozygotes | 1.2 (0.5–2.7) | 4.1 (1.9–8.5) | 7.1 (1.8–29) | 4.4 (2.0–9.4) |

[+]"Reference" includes VDR genotypes 22, 23, 33; "Heterozygotes" includes 12, 13; "Homozygotes" includes 11

TABLE 4-continued

Number of postmenopausal women with fractures and
Odds Ratios for fractures according to
combined VDR haplotype 1 and COLIA1 genotype

| | COLIA1 genotype | | | |
|---|---|---|---|---|
| VDR genotype* | GG | GT | TT | GT + TT |

*Odds Ratios were calculated with women with both the VDR haplotype 1 reference genotype and the COLIA1 GG genotype as reference group. Based on the small numbers of the COLIA1 TT genotype group and the similar trends we observed for the COLIA1 GT and the COLIA1 TT genotype groups, we calculated Odds Ratios for the combined COLIA1 GT + TT genotype group.
†Zero cases in the cell precluded the calculation of the Odds Ratio in the COLIA1 TT genotype group.

References

1. Kanis J A, Melton L J, Christiansen C, Johnston C C, and Khaltaev N. The diagnosis of osteoporosis. J Bone Miner Res 1994;9:1137–41.
2. Smith D M, Nance W E, Kang K W, Christian J C, Johnston C C. Genetic factors in determining bone mass. J Clin Invest 1973;80:2800–08.
3. Pocock N A, Eisman J A, Hopper J L, Yeates M G, Sambrook P N, Ebert S. Genetic determinants of bone mass in adults: a twin study. J Clin Invest 1987;80:706–10.
4. Evans R A, Marel G M, Lancaster E K, Kos S, Evans M, Wond S Y P. Bone mass is low in relatives of osteoporotic patients. Ann Intern Med 1988;109:870–3.
5. Seeman E, et al. Reduced bone mass in daughters of women with osteoporosis. N Engl J Med 1989;320:554–8.
6. Soroko S B, et al. Family history of osteoporosis and bone mineral density at the axial skeleton: The Rancho Bernardo study. J Bone Miner Res 1994;9:761–9.
7. Morrison N A, et al. Prediction of bone density from vitamin D receptor alleles. Nature 1994;367:284–7.
8. Cooper G S, Umbach D M. Are vitamin D receptor polymorphisms associated with bone density ?J Bone Miner Res 1996;11:1841–9.
9. Grant S F A, Reid D M, Blake G, Herd R, Fogelman I, Ralston S H. Reduced bone density and osteoporotic vertebral fracture associated with a polymorphic SpI binding site in the collagen type Iα1 gene. Nat Genet 1996;14:203–5.
10. Uitterlinden A G, et al. Relation of alleles at the collagen type Iα1 gene to bone density and risk of osteoporotic fracture in postmenopausal women. New Engl J Med 1998;338:1016–21.
11. Uitterlinden A G, et al. A large scale population based study of the association of vitamin D receptor gene polymorphisms with bone mineral density. J Bone Miner Res 1996; 11:1242–8.
12. Gueguen R, et al. Segregation analysis and variance components analysis of bone mineral density in healthy families. J Bone Miner Res 1995;12:2017–22.
13. Livshits G, Pavlovsky O, Kobyliansky E. Population biology of human aging: segregation analysis of bone age characteristics. Hum Biol 1996;68:539–54.
14. Kelly P J, et al. Genetic factors in bone turnover. J Clin Endocrinol Metab 1991;72:808–13.
15. Tokita A, et al. Genetic influences on type I collagen synthesis and degradation:
further evidence for genetic regulation of bone turnover.
J Clin Endocrinol Metab 1994;78:1461–6.
16. Garnero P, Arden N K, Griffiths G, Deltnas P D, Spector T D. Genetic influence on bone turnover in postmenopausal twins. J Clin Endocrinol Metab. 1996;81:140–6.
17. White C P, et al. Vitamin D receptor alleles predict osteoporotic fracture risk. Abstract J Bone Miner Res 1994;9(suppl1):S263.
18. Houston L A, Grant S F A, Reid D M, Ralston S H. Vitamin D receptor polymorphism, bone mineral density, and osteoporotic vertebral fracture: studies in a UK population. Bone 1996;18:249–52.
19. Berg J P, Falch J A, Haug E. Fracture rate, pre- and postmenopausal bone loss are not associated with vitamin D receptor genotype in a high-endemic area of osteoporosis. Eur J Endocrinol 1996;135:96–100.
20. Slack J L, DeAnn J L, Bornstein P. Regulation of expression of the type I collagen genes. Am J Med Genet 1993;45:140–51.
21. Pavlin D, et al. Analysis of regulatory regions in the COLIA1 gene responsible for 1,25-dihydroxyvitamin $D_3$-mediated transcriptional repression in osteoblastic cells. J Cell Biochem 1994;56:490–501.
22. Haussler M R, et al. The nuclear vitamin D receptor: biological and molecular regulatory properties revealed. J Bone Miner Res 1998;13:325–49.
23. Hobson B E, Grant S F A, Ralston S H. The functional effects on SpI binding and allele specific transcription of a collagen 1α(I)(COLIA1) polymorphism. Bone 1998;22:10S (abstract)
24. Hofman A, Grobbee D E, de Jong, P T V M, van den Ouweland F A. Determinants of disease and disability in the elderly: the Rotterdam Elderly Study. Eur J Epidemiol 1991;7:403–22.
25. Burger H, et al. The association between age and bone mineral density in men and women aged 55 years and over: The Rotterdam Study. Bone Miner 1994;25:1–13.
26. Burger H, et al. Vertebral deformities and functional impairment in men and women. J Bone Miner Res 1997;12:152.
27. Morrison et al., *PNAS* 89 6665–6669 (1992).
28. Gennari et al., *Calcif Tissue Int* 61 460–463 (1997)

We claim:

1. A method of determining susceptibility to bone fracture in a subject said method comprising analyzing genetic material of a subject to determine the presence of the baT haplotype of the vitamin D receptor gene, wherein the presence of the baT haplotype is indicative of an increased susceptibility to bone fracture.

2. A method of determining susceptibility to bone fracture according to claim 1 said method further comprising determining the presence of a G to T polymorphism at the Sp1 site of the collagen Iα1 gene, wherein detection of said polymorphism is indicative of an increased susceptibility to bone fracture.

3. A method of determining susceptibility to bone fracture according to claim 1 said method further comprising determining the copy number of the b, a or T alleles of the vitamin D receptor gene and/or the s allele of the collagen Iα1 gene.

4. A method according to claim 3 comprising comparing the allele(s) present in the genetic material of the subject with genotypes of the vitamin D receptor or collagen Iα1 genes having known degrees of risk of bone fracture.

5. A method according to claim 2, further comprising determining calcium levels in a subject.

6. A method according to claim 5 wherein daily calcium intake is measured.

7. A method according to claim 1, wherein said method is performed in vitro.

8. A method according to claim 7, wherein said method is performed on blood, or tissue samples of a subject.

9. A method of treating a subject to reduce the risk of bone fracture comprising analysing genetic material of a subject to determine the presence of the baT haplotype of the vitamin D receptor gene, wherein the presence of the baT haplotype is indicative of an increased susceptibility bone fracture, and treating the subject to reduce the risk of bone fracture if the subject has the baT haplotype.

10. A method according to claim 9, wherein suitable treatments include modifications to lifestyle, regular exercise, changes in diet or pharmaceutical preparations.

11. A method according to claim 1, wherein the subject is a mammal.

12. A method according to claim 11, wherein the subject is a human.

13. A method according to claim 11 or 12, wherein the subject is a female.

14. A method of formulating a treatment regimen to decrease the risk of bone fracture, said method comprising analysing genetic material of a subject to determine the presence of the baT haplotype of the vitamin D receptor gene, wherein said haplotype is associated with risk of bone fracture, and formulating a treatment regimen to decrease the risk of bone fracture based on said haplotype.

15. A method according to claim 14, further comprising determining the presence of a G to T polymorphism at the Sp1 site of the collagen Iα1 gene.

16. A method according to claims 14 or 15 further comprising administering the appropriate treatment.

17. A method of determining susceptibility to bone fracture in a subject comprising determining whether the baT haplotype of the vitamin D receptor gene is present in a subject, wherein said determining step utilizes a kit and, wherein said kit comprises (i) one or more nucleic acid primer molecules for amplification of a portion of the vitamin D receptor gene, and (ii) means for determining whether the baT haplotype of said gene is present, and wherein presence of the baT haplotype in the subject is indicative of susceptibility to bone fracture.

18. The method according to claim 17 further comprising the step of determining whether the s allele of a collagen Iα1 gene is present in the subject, said kit further comprising (i) one or more nucleic acid primer molecules for amplification of a portion of the collagen Iα1 gene and (ii) means for determining whether the s allele of the collagen Iα1 gene is present.

19. A method according to claim 1, wherein the haplotype is determined by amplification of a portion of the vitamin D receptor gene between exon 7 and the 3' UTR, followed by restriction enzyme digestion; or any other technique suitable for determining the genotype of a subject.

20. A method according to claim 2, wherein the haplotype is determined by amplification of a portion of the vitamin D receptor gene between exon 7 and the 3' UTR, or amplification of the first intron of the collagen Iα1 gene, followed by restriction enzyme digestion; or any other technique suitable for determining the genotype of a subject.

* * * * *

UNITED STATES PATENT AND TRADEMARK OFFICE
CERTIFICATE OF CORRECTION

PATENT NO. : 6,803,197 B1
DATED : October 12, 2004
INVENTOR(S) : A.G. Uitterlinden et al.

It is certified that error appears in the above-identified patent and that said Letters Patent is hereby corrected as shown below:

Title page,
Item [30], Foreign Application Priority Data, "9819769" should read -- 9819769.2 --
Item [57], ABSTRACT,
Line 10, "die" should read -- the --
Line 10, "SpI" should read -- *Sp*1 --

Column 1,
Line 18, "disease effects" should read -- disease affects --
Line 24, "South-America." should read -- South America. --
Line 53, "studies, focussing" should read -- studies focussing --
Line 57, "SpI" should read -- *Sp*1 --
Line 59, "protein, was" should read -- protein was --

Column 2,
Line 19, "(i.e. the" should read -- (i.e., the --

Column 3,
Line 59, "Ala" should read -- A/a --
Lines 64-65, "allele (s)" should read -- allele(s) --

Column 4,
Lines 21 and 27, "SpI" should read -- *Sp*1 --
Line 42, "agenetic" should read -- genetic --
Line 45, "et al" should read -- et al. --

Column 5,
Line 53, "art Examples" should read -- art. Examples --

UNITED STATES PATENT AND TRADEMARK OFFICE
CERTIFICATE OF CORRECTION

PATENT NO.   : 6,803,197 B1
DATED        : October 12, 2004
INVENTOR(S)  : A.G. Uitterlinden et al.

It is certified that error appears in the above-identified patent and that said Letters Patent is hereby corrected as shown below:

Column 6,
Lines 6 and 55, "SpI" should read -- *Sp*1 --
Line 57, "techniques for" should read -- techniques, for --
Line 60, "for example" should read -- for example, --

Column 7,
Line 3, "couagen" should read -- collagen --
Line 14, "sample, for" should read -- sample for --
Line 40, "(p=0.009)" should read -- (p=0.009), --
Line 60, "SpI" should read -- *Sp*1 --
Line 65, "genotype we" should read -- genotype, we --

Column 8,
Line 14, "than the" should read -- than had the --
Line 15, "group and" should read -- group, and --
Line 25, "in aft the" should read -- in the --
Line 53, "we genotype" should read -- we found that VDR genotype --
Line 58, "change indicating" should read -- change, indicating --

Column 9,
Lines 8, 17 and 19, "SpI" should read -- *Sp*1 --

Column 10,
Line 38, "SpI" should read -- *Sp*1 --

Column 13,
Line 41, "density ?J" should read -- density? J --
Line 45, "SpI" should read -- *Sp*1 --

UNITED STATES PATENT AND TRADEMARK OFFICE
CERTIFICATE OF CORRECTION

PATENT NO. : 6,803,197 B1
DATED : October 12, 2004
INVENTOR(S) : A.G. Uitterlinden et al.

It is certified that error appears in the above-identified patent and that said Letters Patent is hereby corrected as shown below:

Column 14,
Lines 11-14, do not break and appropriately indent "15. Tokita A, et al. Genetic influences on type I collagen synthesis and degradation: further evidence for genetic regulation of bone turnover. J Clin Endocrinol Metab 1994;78:1461-6."
Line 39, "SpI" should read -- *Sp*1 --

Column 15,
Line 42, "subject said" should read -- subject, said --
Lines 48 and 53, "1 said" should read -- 1, said --
Line 67, "blood, or tissue" should read -- blood or tissue --

Signed and Sealed this

Eighth Day of February, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<221> NAME/KEY: misc_feature
<223> OTHER INFORMATION: primer

```
<400> SEQUENCE: 1
caaccaagac tacaagtacc gcgtcagtga                                    30

<210> SEQ ID NO 2
<211> LENGTH: 24
<212> TYPE: DNA
<213> ORGANISM: Artificial Sequence
<220> FEATURE:
<221> NAME/KEY: misc_feature
<223> OTHER INFORMATION: primer

<400> SEQUENCE: 2
gcaactcctc atggctgagg tctc                                          24

<210> SEQ ID NO 3
<211> LENGTH: 30
<212> TYPE: DNA
<213> ORGANISM: Artificial Sequence
<220> FEATURE:
<221> NAME/KEY: misc_feature
<223> OTHER INFORMATION: primer

<400> SEQUENCE: 3
taacttctgg actatttgcg gactttttgg                                    30

<210> SEQ ID NO 4
<211> LENGTH: 20
<212> TYPE: DNA
<213> ORGANISM: Artificial Sequence
<220> FEATURE:
<221> NAME/KEY: misc_feature
<223> OTHER INFORMATION: primer

<400> SEQUENCE: 4
gtccagccct catcctggcc                                               20
```